(12) United States Patent
Hamann (10) Patent No.: US 6,449,042 B1
(45) Date of Patent: Sep. 10, 2002

(54) METHOD AND APPARATUS FOR PARTICLE ASSESSMENT USING MULTIPLE SCANNING BEAM REFLECTANCE

(75) Inventor: Oliver Hamann, Sammamish, WA (US)

(73) Assignee: Laser Sensor Technology, Inc.

(*) Notice: Subject to any disclaimer, the term of this patent is extended or adjusted under 35 U.S.C. 154(b) by 0 days.

(21) Appl. No.: 09/565,626

(22) Filed: May 4, 2000

Related U.S. Application Data (60) Provisional application No. 60/132,480, filed on May 4, 1999.

(51) Int. Cl.[7] .............................................. G01N 21/00
(52) U.S. Cl. ...................................... 356/339; 356/342
(58) Field of Search ................................. 356/335–343

(56) References Cited

U.S. PATENT DOCUMENTS

| | | | |
|---|---|---|---|
| 4,387,993 A | | 6/1983 | Adrian ........................ 356/336 |
| 4,506,979 A | * | 3/1985 | Rogers ....................... 356/28.5 |
| 4,854,705 A | | 8/1989 | Bachalo ...................... 356/336 |
| 4,906,094 A | | 3/1990 | Ashida ........................ 356/336 |
| 5,012,118 A | | 4/1991 | Preikschat et al. .......... 250/574 |
| 5,047,653 A | * | 9/1991 | Garcia et al. ............... 250/574 |
| 5,168,401 A | | 12/1992 | Edriz ........................... 359/625 |
| 5,644,388 A | | 7/1997 | Maekawa et al. ............ 356/73 |
| 5,748,305 A | | 5/1998 | Shimono et al. ............ 356/237 |
| 5,751,423 A | * | 5/1998 | Traina et al. ............... 356/338 |
| 5,790,246 A | | 8/1998 | Kuhnell et al. ............. 356/72 |
| 5,815,264 A | * | 9/1998 | Reed et al. ................. 356/336 |

\* cited by examiner

*Primary Examiner*—Michael P. Stafira
(74) *Attorney, Agent, or Firm*—Graybeal Jackson Haley, LLP (57) ABSTRACT

The present invention relates to a backscattering apparatus and method for optical scanning along a circular path using one or more optical illuminators and receivers. More particularly, it relates to an apparatus and method of focusing one or more beams of light into one or more beam spots, scanning the common beam spot(s) across a circular path and receiving light backscattered from the beam spot(s) with one or more detectors. A rotationally mounted scanning optics having an optical axis parallel to but not coaxial with the axis of rotation is used to accomplish these functions. A motor may be operatively linked to the scanning optics to cause the same to rotate at a constant angular velocity whereby, with appropriate signal generating detector and signal processing electronics, the number and size of particles suspended in a fluid medium exposed to the beam spot(s) can be determined.

28 Claims, 7 Drawing Sheets

METHOD AND APPARATUS FOR PARTICLE ASSESSMENT USING MULTIPLE SCANNING BEAM REFLECTANCE

This application claims the benefit of provisional application 60/132,480 filed May 4, 1999.

FIELD OF THE INVENTION

The present invention relates to an apparatus and method for optical scanning along a circular path. More particularly, it relates to an apparatus and method of focusing one or more beams of light into one beam spot, scanning this common beam spot across a circular path and receiving light backscattered from this beam spot with one or more detectors. An application of the present invention includes a method for analyzing the number and size of particles suspended in a fluid medium.

BACKGROUND OF THE INVENTION

The technology disclosed in U.S. Pat. No. 4,871,251 has successfully shown the use of a scanning device to analyze the number and size of particles suspended in a fluid medium. Using the device presented therein, it is possible to characterizes particles in a size range between approximately 1 μm and 1000 μm over a wide range of concentrations by means of measuring the time duration of light backscattered from individual particles inside the fluid medium. However, in the practical use of the patented device it has been found that simultaneous illumination with light of different wavelengths and the analysis of the spectrum of backscattered light could greatly enhance the use of the device.

Instruments defining the current state of the art fall into two categories. One group of optical instruments is concerned with the chemical analysis of ensembles of particles in a fluid medium (Raman spectrometers, Near Infrared spectrometers, and others). These instruments typically do not allow an analysis of individual particles and provide no number or size measurements of individual particles. A second group of instruments analyzes the size and/or number of particles in a fluid medium, either by forward scattering of light (Laser Diffraction Particle Sizers) or measurement of the amount of backscattered light from either an ensemble of particles or individual particles. No simultaneous measurement of chemical composition and size and number of individual particles is available from instruments of this group. The present invention seeks to overcome this limitation.

SUMMARY OF THE INVENTION

The present invention shows a novel arrangement for a rotating scanning optics that allows the use of one or more independent illumination and receiving beams, all being focused at the same scanning spot. This scanning spot follows a circular scan path in a plane perpendicular to the axis of rotation of the scanning optics. In addition to the advantages this new arrangement has over the present device based upon that disclosed in U.S. Pat. No. 4,871,251, many other optically scanning devices can benefit from the present arrangement.

The present invention allows the construction of an apparatus for simultaneously analyzing the number, size and chemical composition of individual particles suspended in a fluid medium. The invention is based on the fact that all rays or beams of light entering a focusing lens parallel to its optical axis will be focused at the focal point of the lens on the optical axis.

In the basic form of the apparatus, a first collimated beam of light is focused by the scanning optics into a focal plane. A second collimated receiving beam parallel to the first beam is focused by the same optics into the same focal spot. Both collimated beams are parallel to the optical axis of the scanning optics. The scanning optics can be a single focusing lens or comprise several optical elements that focus incoming light. Using a real focusing lens or lens system, it is not possible to focus incoming light into a single point. Instead the focused beam will form a waist, the smallest waist diameter is determined by the diffraction limit of the focusing optics (Born, Wolf, *Principles of Optics*). The intersection of the illuminating and receiving beams after passing through the scanning optics defines a measurement volume. The dimensions of this measurement volume are determined by the dimensions of the beam waists of the two focused beams and the intersection angle.

An object that enters the measurement volume is illuminated by the light of the first beam and light will be scattered in all directions. Part of the light falls into the aperture of the second beam and is directed to a detector. If the object enters the illuminating beam outside the measurement volume, no light will be received by the detector.

If the scanning lens is rotated around an axis parallel to its optical axis the measurement volume will scan along a circular path in a scanning plane perpendicular to the axis of rotation. The radius of this circular scanning path is equal to the distance between the optical axis and the rotational axis of the scanning lens. Independent of the angular position of the scanning lens, the two beams always form the measurement volume by intersection; the intersection angle changes slightly along the path.

In a preferred embodiment designed to analyze particles suspended in fluid medium, the optics forming the two collimated beams and the scanning lens are arranged inside an enclosure and the beams fall through an optical window into the fluid medium. The position of the window is chosen so that the focal plane of the scanning lens lays within the fluid medium outside the enclosure.

If the scanning lens rotates with constant angular velocity, the measurement volume will scan through the fluid medium with constant tangential velocity along the circular scanning path. Particles in the fluid medium will enter the scanning path at random locations. The dimension of the scanning volume should be smaller than the size of particles to be analyzed. The measurement volume scans across the surface of a particle suspended in the fluid medium if it enters into the scanning path. For a scanning circle diameter that is much larger than the size of the scanned particle the path across the particle will be almost linear. The length of this path depends on where the particle is hit by the scanning measurement volume and will be between almost zero and the longest linear distance between two points on the surface of the particle. The scanning path across the particle is called a chord. While the measurement volume scans across the particle surface, light backscattered from the particle falls into the receiving optics, guided to a detector and the detector signal is recorded by electronic means. If the relative speed of the scanning measurement volume with respect to the particle is known, the length of the scanned chord is determined by multiplying the relative velocity with the measured time duration of the backscattered light signal. An example of electronics suitable for this task is disclosed in U.S. Pat. No. 4,871,251, which is incorporated herein by reference.

Depending on the application of the apparatus, illuminating beams can have different wavelengths of light; different diameters of beams lead to different illuminating or receiving apertures.

DETAILED DESCRIPTION OF THE INVENTION

To increase understanding of the invention, the principles of the invention are disclosed by means of an example of an embodiment using only one illuminating and one receiving bundle of rays or beams. A preferred embodiment for analyzing the number and size of particles suspended in a fluid is also disclosed. A more complex embodiment comprising multiple illuminating and receiving beams will be described thereafter.

Figure 1:
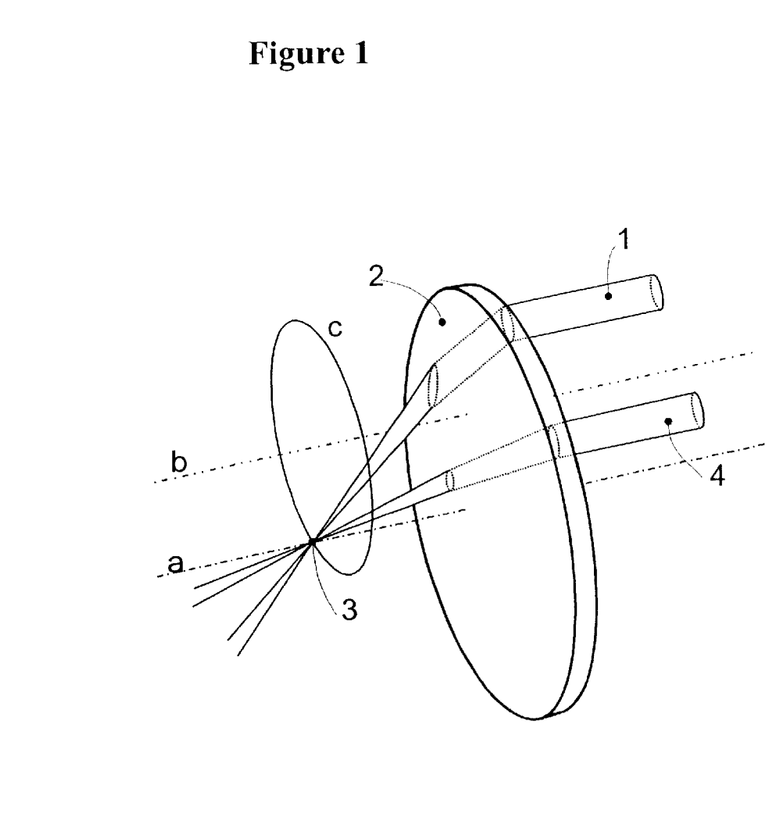
FIG. 1 is a perspective view of a focusing lens according to the present invention focusing two beams into a common focal spot.
Figure 2:
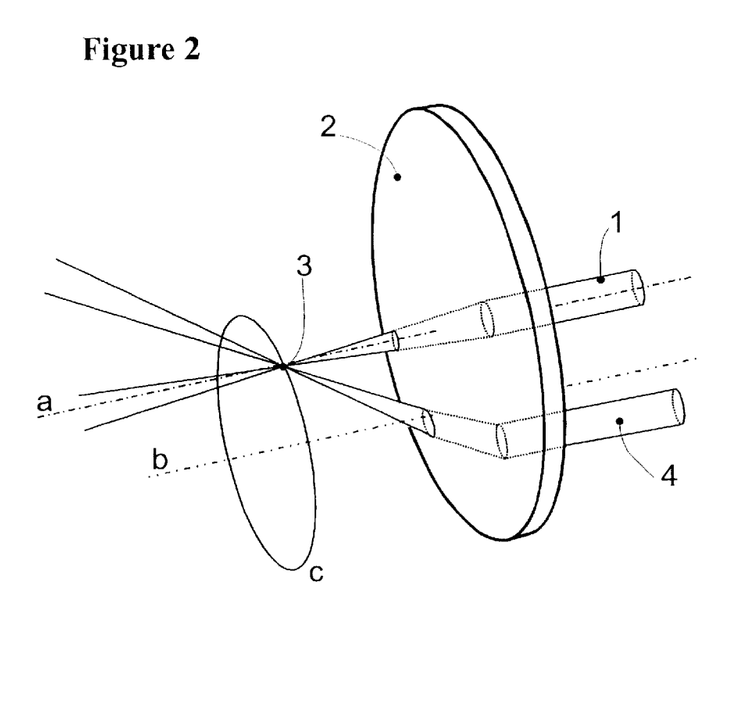
FIG. 2 is a perspective view of the lens of FIG. 1 rotated about a mechanical axis.

FIGS. 1 and 2 show schematically a lens 2 and its optical axis a. A first bundle of rays 1, parallel to the optical axis a, is focused into the focal spot 3 on the optical axis. A second bundle of rays 4, also parallel to the optical axis a, enters the lens at a location different then bundle 1 but is focused into the same focal spot 3. Additional parallel bundles of rays would all be focused into the same focal spot. If lens 2 is rotated around a mechanical axis b parallel to but not collinear with the optical axis a as shown in FIG. 2 all bundles of rays are still focused in one common focal spot 3. However, upon rotating lens 2 around axis b, the location of the focal spot 3 will change. The focal spot will follow a circular path c in a scanning plane perpendicular to the axis of rotation b.

If 2 is a bundle of illuminating rays, an object located at the focal spot will scatter light into all directions; a portion of the scattered light is collected by lens 2 and collimated into the receiving bundle of rays 4. As the lens 2 is rotated around axis b, the focal spot 3 will scan over objects located on the circular scan path c. Whenever the focal spot hits one of the objects, light will be backscattered into the receiving bundle 4. Obviously this concept can be expanded to having several illuminating and receiving ray bundles or beams, all being focused into the same scanning spot, depending upon the nature of lens 2.

Figure 3:
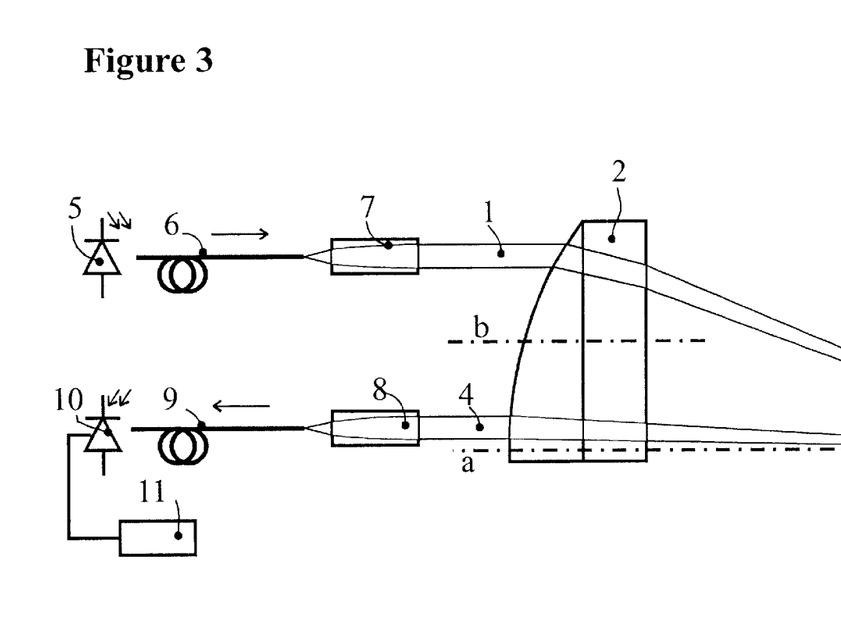
FIG. 3 is a cross-sectional view of a preferred embodiment of the present invention showing an illuminating and receiving optical system so that the scanning lens focuses their respective beams into a common focal spot.
Figure 3A:
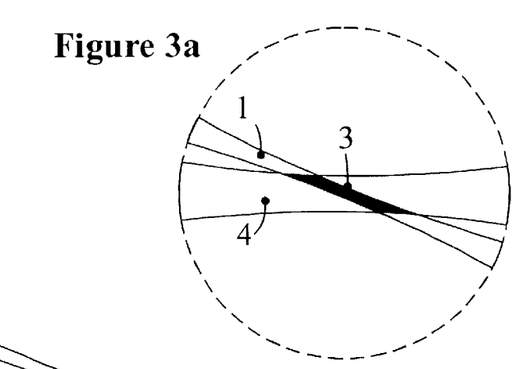
FIG. 3a is an enlargement of the focal spot area of FIG. 3.

FIG. 3 shows a preferred embodiment of the present invention. Light from an optical source 5, preferably a laser diode, is launched into an optical fiber 6. The light is guided to an optics 7 that forms the collimated illuminating beam 1. This beam of light is focused by the scanning lens 2 into the focal spot on the optical axis a of lens 2. The second collimating optics 8 defines a beam 4, also focused by lens 2 into a focal spot on the optical axis a. The beams 1 and 4 intersect and form the measurement volume 3 shown in the enlargement in FIG. 3a. A particle that enters the measurement volume 3 will scatter light in all directions. Backscattered light that falls into the aperture defined by beam 4 will be received by the optics 8 and coupled into a fiber 9. Fiber 9 guides the received scattered light to a detector 10 that converts the optical signal into electrical signals. The electrical signal is then processes by a detector electronics 11.

FIG. 3 also shows gradient index lenses as collimating optics 7 and 8. Other collimating lens arrangements are also possible. The scanning lens 2 is shown as a simple plano-convex lens for ease of drawing. To achieve small focal spot sizes and therefore a small measurement volume it is necessary to use a better spherically corrected lens design. Possibilities include best form lenses, achromats, aspheres, or optics with multiple elements.

Figure 4:
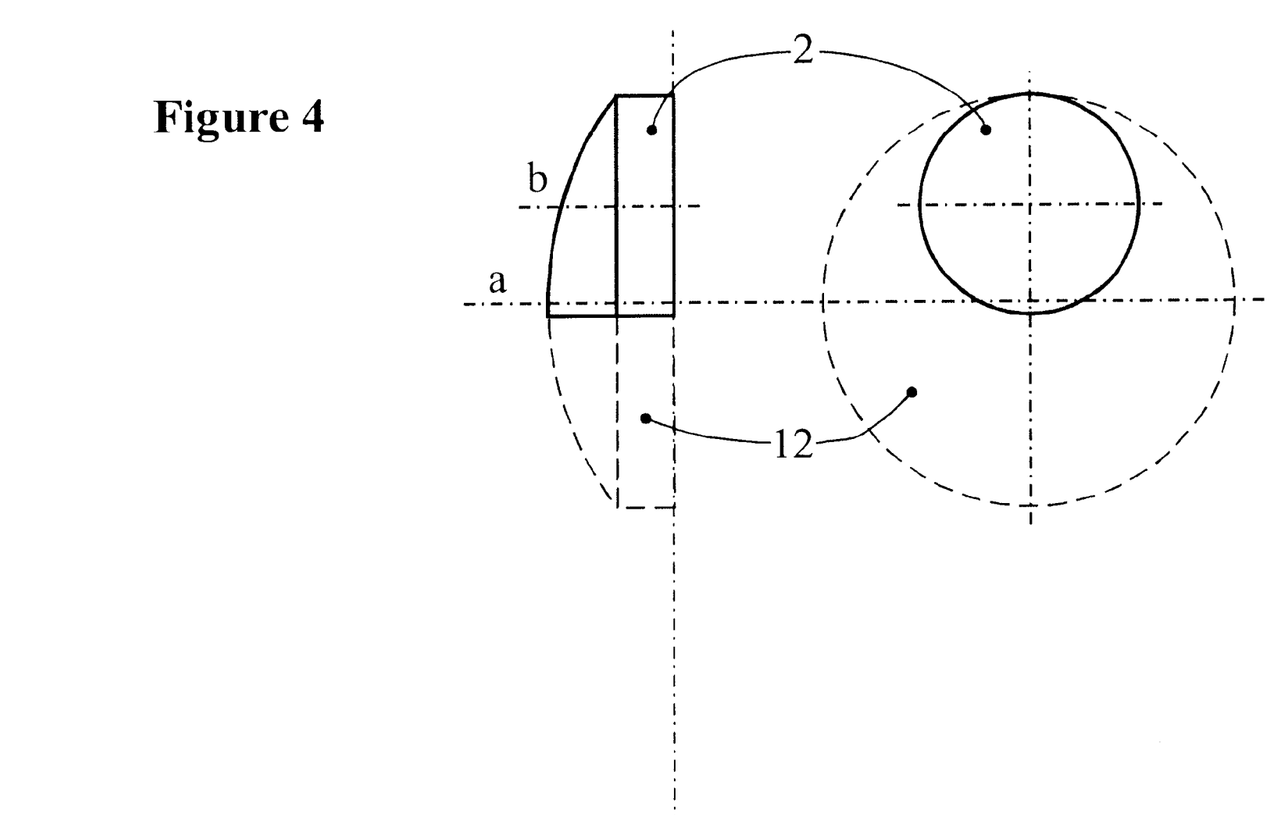
FIG. 4 shows a possible way of cutting a scanning lens off-center from a larger lens.

Lastly, the scanning lens 2 of FIG. 3 has to be rotated around the mechanical axis b. FIG. 4 shows a possible location of the mechanical axis b and the optical axis a. The scanning lens 2 is cut from a larger lens 12 to reduce the weight of the rotating lens and to balance the rotating parts more easily.

Figure 5:
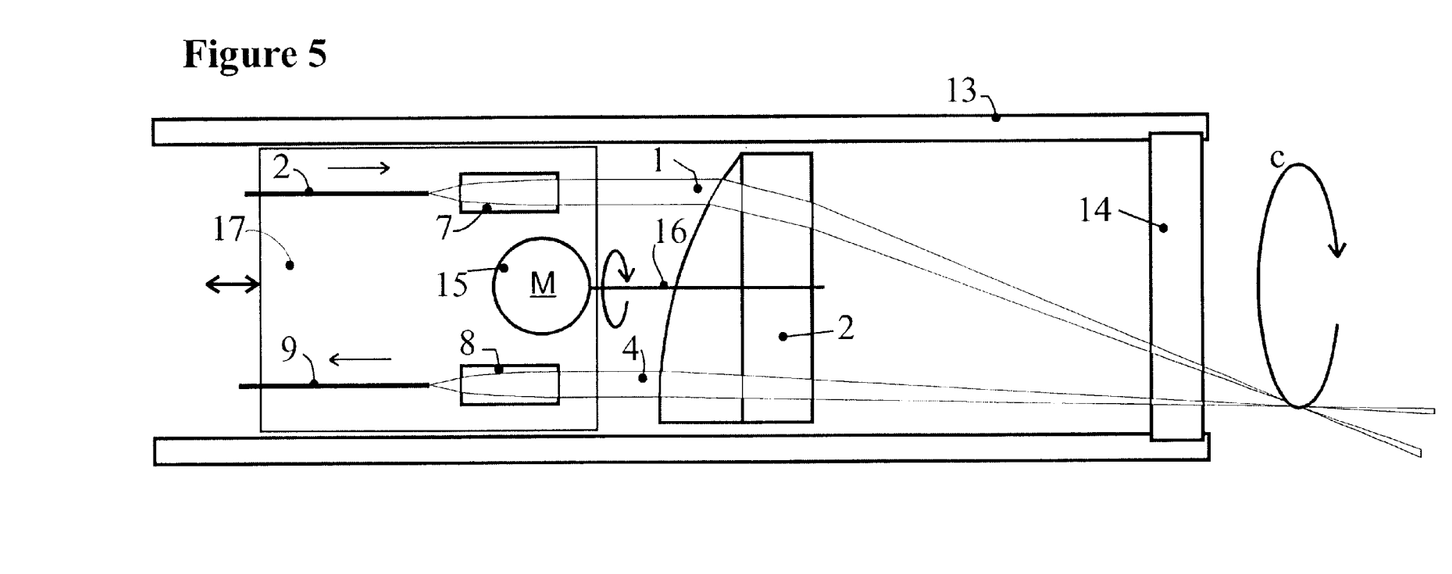
FIG. 5 is a cross-sectional view of the preferred embodiment of FIG. 3 mounted inside an enclosure.
Figure 6A:
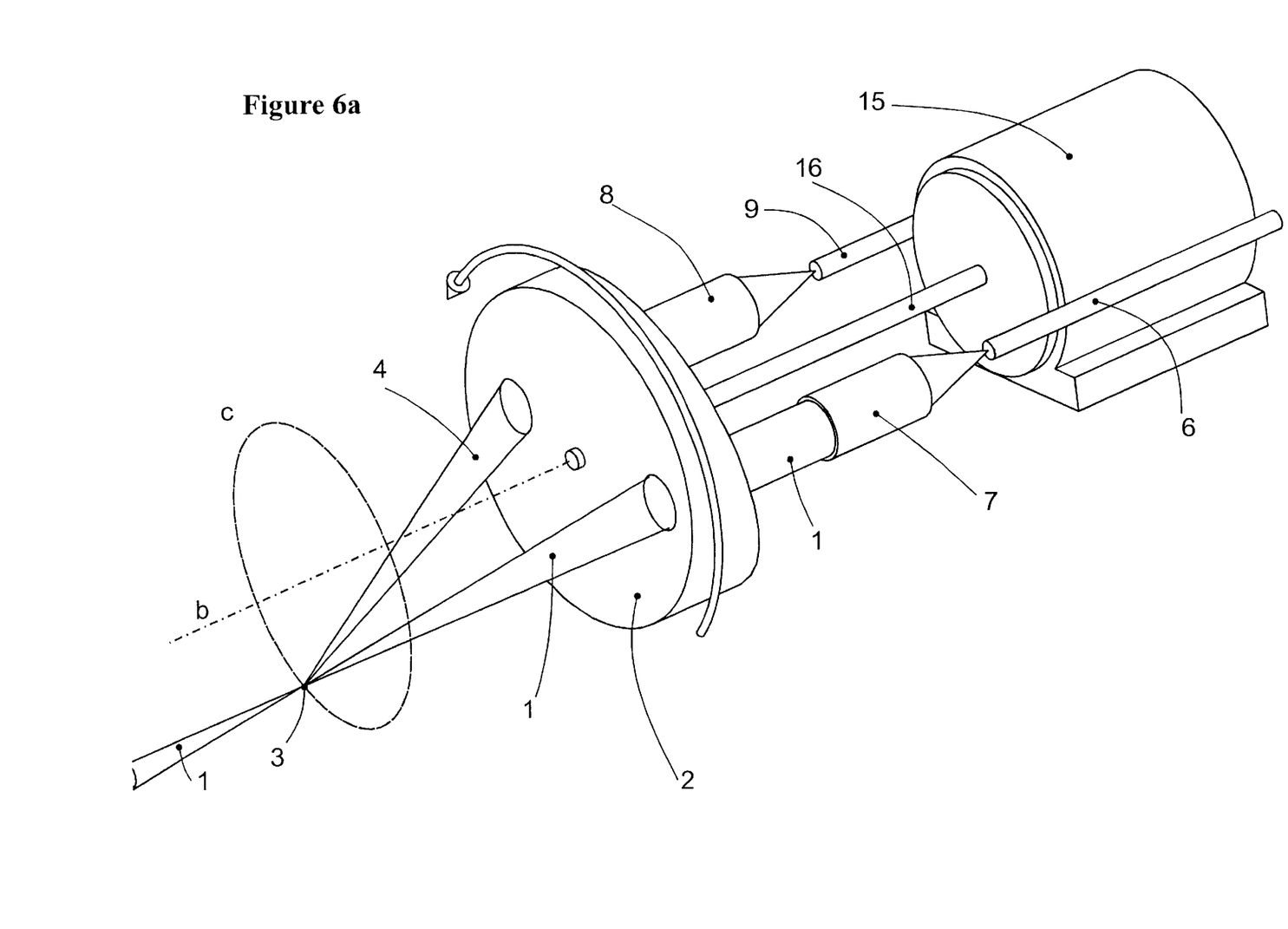
FIG. 6a is a perspective view of the preferred embodiment shown in FIG. 3.
Figure 6B:
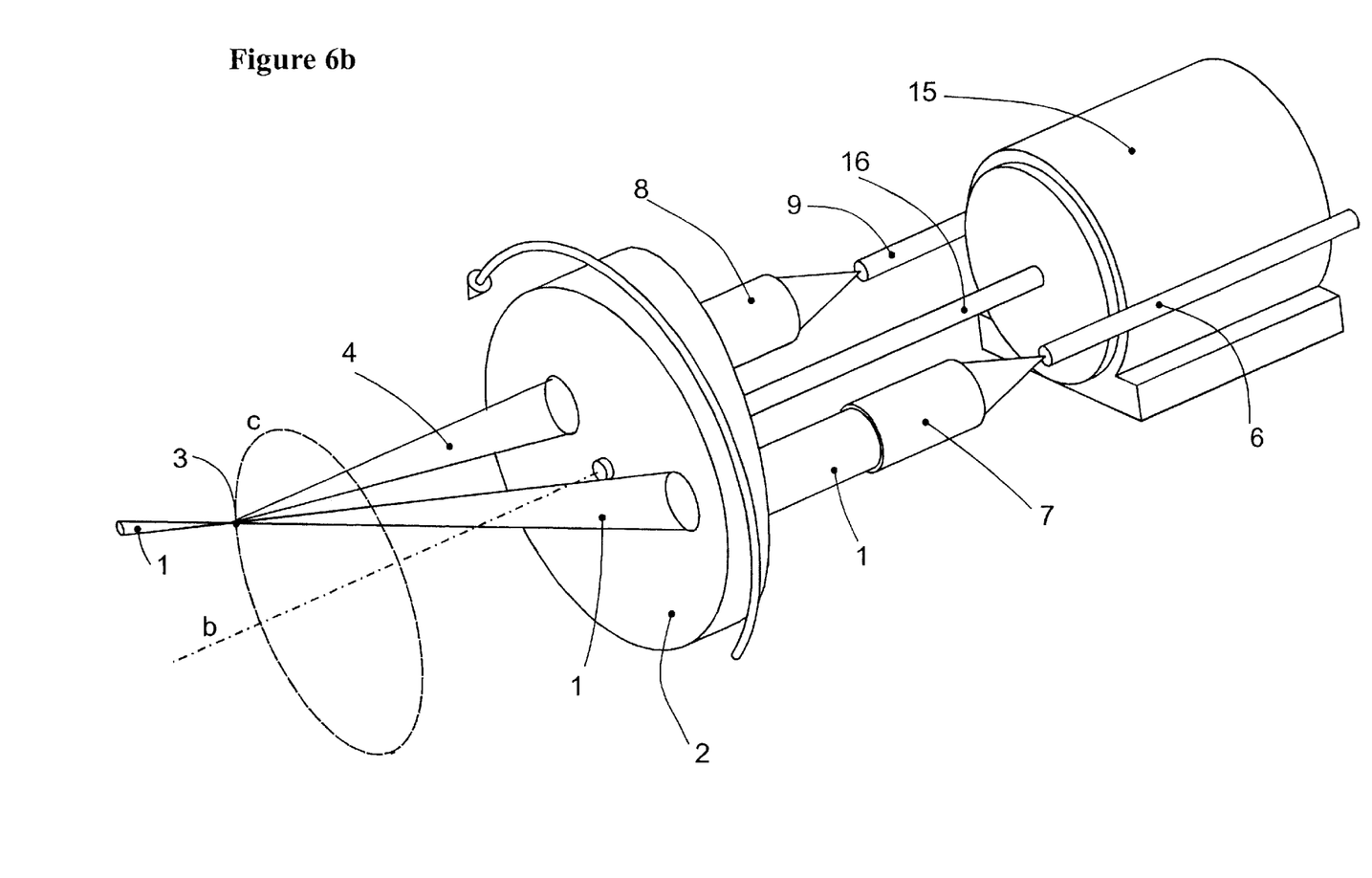
FIG. 6b is a perspective view of the preferred embodiment shown in FIG. 6a after rotation of the scanning lens about the mechanical axis.

FIG. 5 shows the optics of FIG. 3 mounted inside a probe housing 13. The beams 1 and 4 fall through a probe window 14 into the fluid medium outside the probe. A motor 15 drives the shaft 16 to rotate the scanning lens 2. Using an apparatus according to United States patent number 4,871,251, it has been found that it is beneficial to be able to adjust the exact location of a scanning volume 3 with respect to the surface of the optical window 14. FIG. 5 therefore shows the optics arranged on a sliding base 17 that allows the optics to be moved inside the enclosure with respect to the fixed window. FIGS. 6a and 6b show a three dimensional view of the optics presented in FIG. 3. The circle c indicates the scanning path. In FIG. 6a one possible rotational position of the scanning lens 2 is shown. After rotating the scanning lens around axis b for about 270° the lens 2 assumes the position shown in FIG. 6b. The illuminating beam 1 now focuses on another section of the scanning path c. The receiving optics 8 now also observes this spot. When the lens 2 is continuously rotated around axis b the intersection of beams 1 and 4 will scan across all points on the scanning path 17.

In extension of the basic design described above more illuminating and/or receiving optics can be added. Each collimated beam parallel to the optical axis a falling through the scanning lens will be focused on the optical axis a and a section of the focused beam waist will coincide with the beam waists defined by other beams. Each combination of two of those beams defines a specific measurement volume. By using the correct design for the scanning lens all measurement volumes can coincide. When the illuminating beams use light of at least two different wavelengths the scanning optics should be of achromatic or apochromatic design to ensure that all measurement volumes coincide. A possible application for this arrangement using several different illuminating wavelengths is to analyze not only the number and size of particles suspended in a fluid medium but also obtain spectroscopic information and thus draw conclusions about the chemical composition of different types of particles in the medium. If the receiving detector is a spectrometer, spectral information from individual scanned particles can be obtained through one receiving optics, otherwise several receiving optics can be used, each guiding light through a wavelength filter to a separate detector. Other possibilities include simultaneous single particle Raman spectroscopy or single particle fluorescence analysis.

Figure 7:
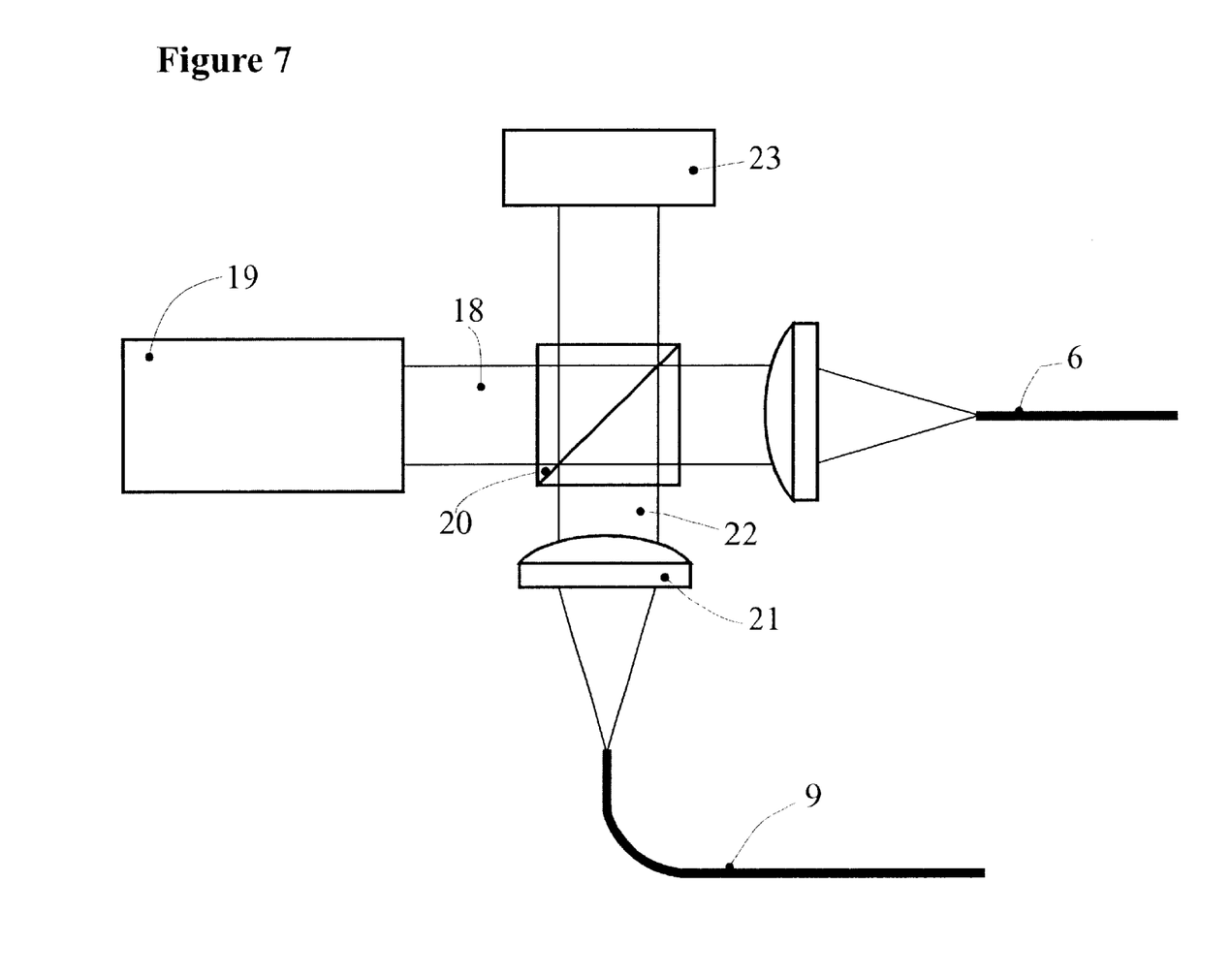
FIG. 7 illustrates the setup of an interferometer as part of the receiving optical system.

Other applications of the rotating scanning optics include those where commonly rotating prisms or mirrors are used. An advantage of the disclosed invention over such systems is that the focal spot scans across a path on a flat plane, whereas the scan paths of mirror or prism scanners usually are on cylindrical surfaces. Especially when objects next to a plane window are to be scanned, the disclosed rotating optics scanner is preferable. Yet another application is the analysis of surface roughness. By using an interferometer, surface roughness on the scale of fractions of the wavelength used in the scanner can be analyzed. FIG. 7 shows an example of an interferometer setup. Collimated light 18 from a sufficiently coherent light source 19 is guided through a beamsplitter 20 and coupled into the optical fiber 6. The arrangement of the scanning optics remains as shown in FIG. 3. Light backscattered from a rough object located in the scanning plane is collected and coupled into the receiving fiber 9. The received light is emitted from fiber 9 and collimated by lens 21 into beam 22. Beam 22 passes through the beamsplitter 19 and interferes with the reflected portion of illuminating beam 18. Depending on the phase relationship of illuminating beam 18 and received beam 22 the detector 23 will receive light of varying intensity as the scanner rotates and the measurement volumes scans across the rough surface. The intensity variations include information about the surface roughness of the scanned object.

INDUSTRIAL APPLICABILITY

The present invention will find utility in the fields of analysis of particles suspended in stationary or moving fluid mediums where such analysis includes the number of particles in a sample, the size of the particles, and chemical composition of the particles.

What is claimed:

1. An apparatus for optical scanning along an essentially circular path, the apparatus having a mechanical base and comprising:
   a plurality of optical sources and an optical systems arranged on the mechanical base to form a plurality of individual collimated illumination beams parallel to a mechanical axis of the apparatus;
   a scanning optics rotationally mounted on the mechanical base to focus each of the collimated illumination beams into one common scanning spot, wherein the axis of rotation is coaxial with the mechanical axis and the scanning optics have an optical axis parallel to but not coaxial with the mechanical axis such that the common scanning spot sweeps a circular scanning path on a scanning plane perpendicular to the mechanical axis when the scanning optics is rotated; and
   a plurality of receiving optical systems arranged on the mechanical base to receive light backscattered from an object located at the scanning spot through the scanning optics, each receiving optical system having an optical axis parallel to the mechanical axis of the apparatus and operatively coupled to a detector arranged to receive the backscattered light and generate a signal proportional to the properties of the received light.

2. The apparatus according to claim 1 wherein the scanning optics is rotated about the mechanical axis by means of a motor at a known angular velocity.

3. The apparatus according to claim 2 where said angular velocity is constant.

4. The apparatus according to claim 1 wherein the scanning optics comprises one or more focusing optical elements.

5. The apparatus according to claim 4 wherein one optical element is an aspheric lens.

6. The apparatus according to claim 4 wherein one of the optical elements is cut off-center from a larger original element.

7. The apparatus according to claim 3 wherein the scanning optics comprise one or more focusing optical elements.

8. The apparatus according to claim 7 wherein one of the optical elements is cut off-center from a larger original element.

9. The apparatus according to claim 1 wherein the receiving optical systems comprise an optical filter to selectively receive light of a defined range of wavelengths.

10. The apparatus according to claim 4 wherein the receiving optical systems comprise an optical filter to selectively receive light of a defined range of wavelengths.

11. The apparatus according to claim 7 wherein the receiving optical systems comprise an optical filter to selectively receive light of a defined range of wavelengths.

12. The apparatus according to claim 8 wherein the receiving optical systems comprise an optical filter to selectively receive light of a defined range of wavelengths.

13. The apparatus of claim 1 wherein at least one of the plurality of optical sources emits light of a unique wavelength.

14. The apparatus of claim 4 wherein at least one of the plurality of optical sources emits light of a unique wavelength.

15. The apparatus of claim 6 wherein at least one of the plurality of optical sources emits light of a unique wavelength.

16. An apparatus for optical scanning along an essentially circular path, the apparatus having mechanical base and comprising:
   at least one optical source and optical system arranged on the mechanical base to form at east one collimated illumination beam parallel to a mechanical axis of the apparatus;
   a scanning optics rotationally mounted on the mechanical base to focus each of the collimated illumination beams into one common scanning spot, wherein the axis of rotation is coaxial with the mechanical axis and the scanning optics have an optical axis parallel to but not coaxial with the mechanical axis such that the common scanning spot sweeps a circular scanning path on a scanning plane perpendicular to the mechanical axis when the scanning optics is rotated; and
   at least one receiving optical system arranged on the mechanical base to receive light backscattered from an object located at the scanning spot through the scanning optics, the receiving optical system having an optical axis parallel to the mechanical axis of the apparatus and operatively coupled to a detector arranged to receive the backscattered light and generate a signal proportional to the properties of the received light.

17. The apparatus according to claim, 16 wherein the scanning optics is rotated about the mechanical axis by means of a motor at a known angular velocity.

18. The apparatus according to claim 16 wherein the scanning optics comprise one or more focusing optical elements.

19. The apparatus according to claim 17 wherein the scanning optics comprises one or more focusing optical elements.

20. The apparatus according to claim 16 wherein the at least one receiving optical system comprises an optical filter to selectively receive light of one or more wavelengths.

21. The apparatus according to claim 16 wherein the scanning optics comprises a focusing optical element that is cut off-center from a larger original optical element.

22. The apparatus according to claim 16 further comprising a housing surrounding the at least one optical source and optical system, the scanning optics, and the at least one receiving optical system; and an optical window whereby the scanning path is located at a plane exteriorly of the housing.

23. The apparatus according to claim 22 wherein the optical window is coplanar with the plane of the scanning path.

24. The apparatus according to claim 22 wherein the distance between the optical window and the plane of the scanning path is adjustable.

25. A method for scanning an area or volume comprising:
  a) mounting at least one optical source and optical system on a mechanical base to form at least one collimated illumination beam parallel to a mechanical axis defined by the mechanical base;
  b) rotationally mounting a scanning optics on the mechanical base to focus each of the collimated illumination beams into one common scanning spot, wherein the axis of rotation is coaxial with the mechanical axis and the scanning optics have an optical axis parallel to but not coaxial with the mechanical axis such that the common scanning spot sweeps a circular scanning path on a scanning plane perpendicular to the mechanical axis when the scanning optics is rotated; and
  c) mounting at least one receiving optical system on the mechanical base to receive light backscattered from an object located at the scanning spot through the scanning optics, the receiving optical system having an optical axis parallel to the mechanical axis of the apparatus and operatively coupled to a detector arranged to receive the backscattered light and generate a signal proportional to the properties of the received light.

26. The method according to claim 25 further comprising rotating the scanning optics by means of a motor operatively linked to the scanning optics.

27. The method according to claim 25 wherein the scanning optics is selected from the group consisting of best form lenses, achomats, aspheres, and multi-element optics.

28. The method according to claim 25 wherein the illuminating beams use a plurality of wavelengths and the detector is a spectrometer.

* * * * *